(12) United States Patent
Giorgetti

(10) Patent No.: US 6,194,462 B1
(45) Date of Patent: Feb. 27, 2001

(54) PHARMACEUTICAL PREPARATION CONTAINING NIMESULIDE FOR ORAL ADMINISTRATION

(75) Inventor: Paolo Luca Maria Giorgetti, Milan (IT)

(73) Assignee: Errekappa Euroterapici S.p.A., Milan (IT)

(*) Notice: Subject to any disclaimer, the term of this patent is extended or adjusted under 35 U.S.C. 154(b) by 0 days.

(21) Appl. No.: 09/214,023

(22) PCT Filed: Apr. 14, 1998

(86) PCT No.: PCT/IB98/00549

§ 371 Date: Dec. 22, 1998

§ 102(e) Date: Dec. 22, 1998

(87) PCT Pub. No.: WO98/47501

PCT Pub. Date: Oct. 29, 1998

(30) Foreign Application Priority Data

Jun. 20, 1997 (IT) .............................................. RM97A0241

(51) Int. Cl.[7] .................................................. A61K 31/18
(52) U.S. Cl. ............................................................. 514/605
(58) Field of Search ............................................... 514/605

(56) References Cited

U.S. PATENT DOCUMENTS

| | | | |
|---|---|---|---|
| 5,716,609 | * 2/1998 | Jain et al. | 424/78.05 |
| 5,998,480 | 12/1999 | Giorgetti . | |

FOREIGN PATENT DOCUMENTS

| | | |
|---|---|---|
| 801812 | 1/1974 | (BE) . |
| 4116659 | 11/1991 | (DE) . |
| 0 367 382 | 5/1990 | (EP) . |
| 0532900 | 3/1993 | (EP) . |
| 0 843 998 | 5/1998 | (EP) . |
| 2 662 360 | 11/1991 | (FR) . |
| RM96A0480 | 1/1998 | (IT) . |
| 299 500 | 2/1997 | (NZ) . |
| WO 91/17774 | 11/1991 | (WO) . |
| WO 94/28031 | 12/1994 | (WO) . |
| WO 96/11002 | 4/1996 | (WO) . |

OTHER PUBLICATIONS

Munhoz M S L et al: "Estudo Comparativo Entre Nimesulide Versus Diclofenaco Potassico Em Afeccoes Otorrinolaringologicas: Comparative Study With Nimesulide V.S. Potassium Diclofenac in ent Disease" Revista Da Sociedade Brasileira de Medicina Tropical, vol. 47, No. 11, Nov. 1, 1990, pp. 591–594, XP000563507.

Susan Buvadari, et al., eds. *The Merck Index*; (Rahway, New Jersey: Merck & Co., Inc., 1989), 1035.

Dialog Select, The Merick Index Online, CAS Registry No. 51803–78–2 for nimesulide, Dialog File No. 304, Accession No. 006640 (1997).

Analytical Abstracts, Dialog File No. 305, Accession No. 273305 (1997), Abstract for Alvarez–Lueje, A., et al., "Voltammetric Study of Nimesulide and Its Differential Pulse Polarographic Determination in Pharmaceuticals", *Electroanalysis*, 9(15), pp. 1209–1213, (New York, Oct. 1997).

Analytical Abstracts, Dialog File No. 305, Accession No. 269327 (1997), Abstract for Chowdary, K.P.R., et al., "A New Spectrophotometric Method for the Determination of Nimesulide", *Indian Drugs*, 34(7), pp. 396–398, (Jul. 1997).

Analytical Abstracts, Dialog File No. 305, Accession No. 263471 (1997), Abstract for Sarkar, P., et al., "A Unique Metabolite of Nimesulide", *J. Anal. Toxicol.*, 21(3), pp. 197–202 (May–Jun. 1997).

M. Facino, "Antioxidant Profile of Nimesulide, Indomethacin and Diclofenac in Phosphatidylcholine Liposomes (PCL) as Membrane Model," *Int. J. Tiss. Reac.*, vol. 15, No. 6, 1993, pp. 225–234, XP002048767.

G.P. Velo, "The Anti–inflammatory, Analgesic and Antipyretic Activity of Nimesulide in Experimental Models," *Drug Invest.*, vol. 3, Suppl. 2, 1991, pp. 10–13, XP002048768.

M. Tortorici, "Terapia Delle Otiti Esterne Con La Nimesulide (Nimesulide in the Treatment of the External Otitis)," *ACTA Toxicol. Ther.*, vol. 10, No. 2, 1989, pp. 169–177 XP002048769.

S. Veraldi, et al., "Treatment of Erosive Pustular Dermatosis of the Scalp with Nimesulide," *Eur. J. Dermatol.*, vol. 4, No. 4, 1994, pp. 337–338, XP002048770.

* cited by examiner

*Primary Examiner*—William R. A. Jarvis
(74) *Attorney, Agent, or Firm*—Ladas & Parry

(57) ABSTRACT

Pharmaceutical composition containing nimesulide in a hydroalcoholic solution and a mixture of traditional vehicles and excipients for local use and application to the oral and rhinopharyngeal cavity for the treatment of inflammation of oral and rhinopharyngeal mucosae.

54 Claims, No Drawings

PHARMACEUTICAL PREPARATION CONTAINING NIMESULIDE FOR ORAL ADMINISTRATION

This application is a 371 PCT/IB98/00549, filed Apr. 14, 1998.

The subject matter of this invention concerns fluid pharmaceutical preparations containing nimesulide active substance for oral and rino-pharyngeal use.

Nimesulide (4-nitro-2-phenoxy-methan-sulfanilide) is a potent non steroidal anti-inflammatory drug, presently used in the treatment of painful inflammatory conditions due to rheumatoid arthritis, which also possesses antipyretic activity (BE 801812). Compared to the other non steroidal anti-inflammatories, Nimesulide has a better therapeutical ratio, low acute gastrotoxicity and generally good tolerability.

Nimesulide differentiates itself chemically from other NSAID's due to the fact that its functional acidic group consists of the sulfanilide fraction.

Nimesulide is a strongly hydrophobic substance that is practically insoluble in water (solubility in water at room temperature: 0.01 mg/ml).

Nimesulide's scarce water solubility and "wettability" represent serious limitations for its use in pharmaceutical presentations since these problems do not allow satisfactory drug release and constant bioavailability. Hence the difficulty to develop acceptable fluid pharmaceutical presentations.

In order to overcome the disadvantages caused by nimesulide's poor solubility and wettability, it is essential to increase its solubility in water.

Numerous investigations have been carried out for this purpose which have lead to a number of patents (WO 94/28031, MI 91 A 001396) that illustrate the possibility of including nimesulide in cyclodextrins by employing various preparation techniques. The products for inclusion in cyclodextrins are usefully employed in the development of solid oral pharmaceutical formulations, but do not satisfactorily resolve the problems connected with the preparation of fluid or liquid forms.

To date the attention has been mainly concentrated on problems connected with the systemic administration of nimesulide, albeit, similarly to other NSAID's, the local use of this molecule has also been evaluated. In fact, there are studies and patents on the local administration of nimesulide dispersions in rheumatology, dermatology and traumatology (WO 96/11002). Anti-inflammatories in the form of liquids, tinctures and mouthwash solutions can be administered locally for the treatment of various pathologies in odontostomatology (local treatment of periodontal inflammation such as gingivitis and periodontitis, stomatitis, glossitis) and otorhinolaryngology (tonsillitis, pharzyngitis, laryngitis).

Due to nimesulide's chemical and physical characteristics, its use in water based fluid or liquid pharmaceutical preparations is subordinated to the dissolution of the substance, achievable by salification of the sulfanilide group. Such salification is obtained by using strong bases such as alkaline or alkaline-earth hydroxides, aminoacids, e.g. lysine, choline, glycine. Such dissolution process occurs directly during the preparation of the finished product and the soluble intermediate compound obtained does not require prior isolation.

The solutions obtained by nimesulide salification have a high pH which cannot be used in pharmaceutics for oral administration because of possible problems related to an increase in gastric pH.

These problems are less important in the case of local treatment of the oral cavity, in view of the fact that the solution is not swallowed and remains in contact with a restricted application area and for a limited amount of time.

Given the fact that nimesulide is partially soluble in ethanol, its dissolution may be facilitated by using varying ratios of pharmaceutically acceptable hydroalcoholic solutions.

The subject matter of this invention is the description of pharmaceutical compositions containing nimesulide for local application in the form of a mouthwash solution, tincture or liquid.

However, dissolution of nimesulide active substance does not resolve the problems related to the development of liquid or fluid pharmaceutical preparations for local use considering the unfavourable organoleptic characteristics of the solutions obtained.

DETAILED DESCRIPTION OF THE INVENTION

The pharmaceutical compositions according to this invention include nimesulide active substance in solution form and in a mixture of traditional vehicles and excipients as liquid or fluid pharmaceutical forms for local use and application to the oral and oropharyngeal cavities.

The pharmaceutical compositions according to this invention consist of liquids, tinctures and mouthwash solutions.

These compositions contain nimesulide active substance in solution form at concentrations ranging between 0.001% and 10%.

The ingredients of the vehicle are powders, liquids or creamy masses that are soluble in water or in hydroalcoholic solutions, generally used in pharmaceutical and food preparations as solvents, sweeteners, colouring agents, flavouring agents, viscosity enhancers, surfactants, etc.

The pharmaceutical compositions consist of pharmaceutically acceptable vehicle for 90% to 99.999%, prepared according to traditional methods as described, for example, in "Remington's Pharmaceutical Sciences Handbook, Mack. Publ., N.Y., USA".

The invention concerns in particular a fluid pharmaceutical preparation containing nimesulide active substance (CAS No. 51803-78-2) or one of its active derivatives and is characterized by the fact that in the preparation:

nimesulide is present at concentrations from 0.001 to 10% w/v;

the base of the solution is hydroalcoholic; and the solution has a pH of 8±2.

Furthermore, the alcohol may have one or more —OH groups, especially ethyl alcohol and/or glycerine.

The above mentioned preparation may also contain carbohydrates with 3 to 6 C, especially sorbitol and xylitol.

The weight ratio between $H_2O$ and alcohol plus carbohydrates is preferably between 1:25 and 4:1.

If necessary, pH stability is achieved by using a system consisting of acid-salt of the corresponding acid.

The preparation herein is administered in the form of a mouthwash solution or tincture and is indicated for the topical treatment of inflammation of oral and rhinopharyngeal mucosae.

The compositions described herein have shown that it is possible to obtain pharmaceutical forms containing nimesulide in solution form that is acceptable for local application to oral, pharyngeal and laryngeal mucosa, allowing its use in therapeutical areas in which to date there was no possibility of employing an active substance with better pharmacotoxicological characteristics than those of the other antiinflammatory drugs previously used.

The invention is detailed by two examples:

EXAMPLE 1

Nimesulide mouthwash - 0.1%

| Quali-quantitative composition | % weight/volume |
|---|---|
| Nimesulide | 0.100 |
| Ethyl alcohol | 15.000 |
| Sodium hydroxide | 0.080 |
| Sodium bicarbonate | 2.000 |
| Sodium saccharinate | 0.300 |
| Sodium benzoate | 0.500 |
| Lutrol F127* | 0.700 |
| Mint flavouring agent* | 0.500 |
| EDTA $Na_2$ | 0.025 |
| Methylene blue | 0.005 |
| Purified water (q.s. to:) | 100% |

*The presence of these two substances causes yellowing of the polythene containers

EXAMPLE 2

Nimesulide mouthwash - 0.25%

| Quali-quantitative composition | % weight/volume |
|---|---|
| Nimesulide | 0.250 |
| Ethyl alcohol | 10.000 |
| Glycerine | 5.000 |
| Sorbitol | 5.000 |
| Sodium hydroxide | 0.080 |
| Sodium bicarbonate | 2.000 |
| Sodium saccharinate | 0.200 |
| Sodium benzoate | 1.000 |
| Lutrol F127* | 2.000 |
| Mint flavouring agent* | 0.700 |
| EDTA $Na_2$ | 0.025 |
| Methylene blue | 0.005 |
| Purified water (q.s. to:) | 100% |

*The presence of these two substances causes yellowing of the polythene containers

What is claimed is:

1. A liquid pharmaceutical preparation in a solution form having a pH value of 8±2, wherein the preparation consists of nimesulide, water, alcohol, optionally one or more carbohydrates, wherein at least one carbohydrate has 3 to 6 C, optionally one or more coloring agents, optionally one or more sweeteners, optionally one or more flavoring agents, optionally one or more viscosity enhancers, and optionally one or more acids and one or more salts of said acids for pH stability; wherein the alcohol is selected from the group consisting of ethyl alcohol, glycerine, and a mixture of ethyl alcohol and glycerine;
   wherein the nimesulide is present in the preparation at a first concentration from 0.001 to 10% w/v; and wherein the water is present in the preparation at a second concentration of at least 72% w/v.

2. A pharmaceutical preparation as claimed in claim 1, wherein the second concentration is at least 73.74% w/v.

3. A pharmaceutical preparation as claimed in claim 1, wherein the second concentration is at least 79.9992% w/v.

4. A liquid pharmaceutical preparation in a solution form having a pH value of 8±2, wherein the preparation consists of nimesulide, water, alcohol, optionally one or more carbohydrates, wherein at least one carbohydrate has 3 to 6 C, optionally one or more coloring agents, optionally one or more sweeteners, optionally one or more flavoring agents, optionally one or more viscosity enhancers, and optionally one or more acids and one or more salts of said acids for pH stability; wherein the alcohol is selected from the group consisting of ethyl alcohol, glycerine, and a mixture of ethyl alcohol and glycerine; wherein the nimesulide is present in the preparation at a first concentration from 0.001 to 10% w/v; wherein the water is present in the preparation at a second concentration; wherein the alcohol is present in the preparation at a third concentration; and wherein a ratio of the second concentration to the third concentration is at least 73.74:15.

5. A pharmaceutical preparation as claimed in claim 1, wherein the first concentration ranges from 0.1 to 10% w/v.

6. A pharmaceutical preparation as claimed in claim 1, wherein the first concentration ranges from 0.25 to 10% w/v.

7. A pharmaceutical preparation as claimed in claim 4, wherein the first concentration ranges from 0.1 to 10% w/v.

8. A pharmaceutical preparation as claimed in claim 4, wherein the first concentration ranges from 0.25 to 10% w/v.

9. A pharmaceutical preparation as claimed in claim 5, wherein the alcohol is ethyl alcohol.

10. A pharmaceutical preparation as claimed in claim 6, wherein the alcohol is ethyl alcohol.

11. A pharmaceutical preparation as claimed in claim 7, wherein the alcohol is ethyl alcohol.

12. A pharmaceutical preparation as claimed in claim 8, wherein the alcohol is ethyl alcohol.

13. A fluid pharmaceutical preparation in a solution form having a pH value of 8±2, wherein the preparation consists of:
   (a) nimesulide, wherein the nimesulide is present in the preparation at a concentration from 0.001 to 10% w/v;
   (b) water;
   (c) one or more alcohols, wherein at least one alcohol has one or more —OH groups;
   (d) optionally one or more carbohydrates, wherein at least one carbohydrate has 3 to 6 C;
   (e) optionally one or more sweeteners;
   (f) optionally one or more coloring agents;
   (g) optionally one or more flavoring agents;
   (h) optionally one or more acids and one or more salts of said acids for pH stability; and
   (i) optionally one or more viscosity enhancers.

14. A pharmaceutical preparation as claimed in claim 13, wherein the at least one alcohol is selected from the group consisting of ethyl alcohol, glycerine, and a mixture of ethyl alcohol and glycerine.

15. A pharmaceutical preparation as claimed in claim 13, wherein preparation consists of:
   (a) the nimesulide;
   (b) the water;
   (c) the one or more alcohols;
   (d) sodium hydroxide;
   (e) sodium bicarbonate;
   (f) sodium saccharinate;
   (g) sodium benzoate;
   (h) optionally the one or more viscosity enhancers;
   (i) optionally the one or more flavoring agents;
   (j) EDTA $Na_2$;
   (k) the one or more coloring agents;

(l) optionally the one or more sweeteners; and (m) optionally the one or more carbohydrates, wherein at least one carbohydrate is selected from the group consisting of sorbitol, xylitol, and a mixture of sorbitol and xylitol.

16. A pharmaceutical preparation as claimed in claim 13, wherein preparation consists of:
   (a) the nimesulide;
   (b) the water;
   (c) the one or more alcohols;
   (d) optionally sodium hydroxide;
   (e) optionally sodium bicarbonate;
   (f) optionally sodium saccharinate;
   (g) optionally sodium benzoate;
   (h) optionally the one or more viscosity enhancers;
   (i) optionally the one or more flavoring agents;
   (j) optionally EDTA $Na_2$;
   (k) optionally the one or more coloring agents;
   (l) optionally the one or more sweeteners; and
   (m) optionally the one or more carbohydrates, wherein at least one carbohydrate is selected from the group consisting of sorbitol, xylitol, and a mixture of sorbitol and xylitol.

17. A pharmaceutical preparation as claimed in claim 13, wherein preparation consists of:
   (a) the nimesulide;
   (b) the water;
   (c) the one or more alcohols;
   (d) optionally sodium hydroxide;
   (e) optionally sodium bicarbonate;
   (f) optionally sodium saccharinate;
   (g) optionally sodium benzoate;
   (h) optionally the one or more viscosity enhancers;
   (i) optionally a mint flavoring agent;
   (j) optionally EDTA $Na_2$;
   (k) optionally methylene blue;
   (l) optionally the one or more sweeteners; and
   (m) optionally the one or more carbohydrates, wherein at least one carbohydrate is selected from the group consisting of sorbitol, xylitol, and a mixture of sorbitol and xylitol.

18. A pharmaceutical preparation as claimed in claim 15, wherein the at least ore alcohol is ethyl alcohol.

19. A pharmaceutical preparation as claimed in claim 16, wherein the at least one alcohol is ethyl alcohol.

20. A pharmaceutical preparation as claimed in claim 17, wherein the at least one alcohol is ethyl alcohol.

21. A pharmaceutical preparation as claimed in claim 9, wherein the preparation includes the carbohydrate with 3 to 6 C.

22. A pharmaceutical preparation as claimed in claim 21, wherein the carbohydrate is selected from the group consisting of sorbitol, xylitol, and a mixture of sorbitol and xylitol.

23. A pharmaceutical preparation as claimed in claim 4, wherein the preparation includes the carbohydrate with 3 to 6 C.

24. A pharmaceutical preparation as claimed in claim 23, wherein the carbohydrate is selected from the group consisting of sorbitol, xylitol, and a mixture of sorbitol and xylitol.

25. A pharmaceutical preparation as claimed in claim 1, wherein the preparation is a mouthwash solution or tincture.

26. A pharmaceutical preparation as claimed in claim 4, wherein the preparation is a mouthwash solution or tincture.

27. A pharmaceutical preparation as claimed in claim 15, wherein the preparation is a mouthwash solution or tincture.

28. A pharmaceutical preparation as claimed in claim 13, wherein the preparation is a mouthwash solution or tincture.

29. A pharmaceutical preparation as claimed in claim 13, wherein a weight ratio of the water to the alcohol plus the carbohydrates is between 1:25 and 4:1.

30. A method for treating inflammation of oral, pharyngeal, rhinopharyngeal, or laryngeal mucosa, the method comprising:
   topically applying the pharmaceutical preparation claimed in claim 1 to the mucosa.

31. A method for treating inflammation of oral, pharyngeal, rhinopharyngeal, or laryngeal mucosa, the method comprising:
   topically applying the pharmaceutical preparation claimed in claim 4 to the mucosa.

32. A method for treating inflammation of oral, pharyngeal, rhinopharyngeal, or laryngeal mucosa, the method comprising:
   topically applying the pharmaceutical preparation claimed in claim 15 to the mucosa.

33. A method for treating inflammation of oral, pharyngeal, rhinopharyngeal, or laryngeal mucosa, the method comprising:
   topically applying the pharmaceutical preparation claimed in claim 13 to the mucosa.

34. A pharmaceutical preparation as claimed in claim 15, wherein the at least one alcohol is selected from the group consisting of ethyl alcohol, glycerine, and a mixture of ethyl alcohol and glycerine.

35. A pharmaceutical preparation as claimed in claim 16, wherein the at least one alcohol is selected from the group consisting of ethyl alcohol, glycerine, and a mixture of ethyl alcohol and glycerine.

36. A pharmaceutical preparation as claimed in claim 17, wherein the at least one alcohol is selected from the group consisting of ethyl alcohol, glycerine, and a mixture of ethyl alcohol and glycerine.

37. A pharmaceutical preparation as claimed in claim 13, wherein the at least one alcohol is ethyl alcohol.

38. A pharmaceutical preparation as claimed in claim 4, wherein the second concentration is at least 73.74% w/v.

39. A pharmaceutical preparation as claimed in claim 4, wherein the alcohol is ethyl alcohol; and wherein the second concentration is at least 73.74% w/v.

40. A fluid pharmaceutical preparation in a solution form having a pH value of 8±2, wherein the preparation consists of:
   (a) nimesulide, wherein the nimesulide is present in the preparation at a first concentration from 0.001 to 10% w/v;
   (b) water;
   (c) one or more alcohols, wherein at least one alcohol has one or more —OH groups;
   (d) optionally one or more carbohydrates, wherein at least one carbohydrate has 3 to 6 C;
   (e) optionally one or more sweeteners;
   (f) optionally one or more coloring agents;
   (g) optionally one or more flavoring agents;
   (h) optionally one or more acids and one or more salts of said acids for pH stability;
   (i) optionally one or more viscosity enhancers;

(j) optionally sodium hydroxide;

(k) optionally sodium bicarbonate;

(l) optionally sodium saccharinate;

(m) optionally sodium benzoate; and (n) optionally EDTA $Na_2$.

41. A fluid pharmaceutical preparation as claimed in claim 40, wherein the preparation consists of:

(a) the nimesulide;

(b) the water;

(c) the one or more alcohols;

(d) optionally the one or more carbohydrates;

(e) optionally the one or more sweeteners;

(f) optionally the one or more coloring agents;

(g) optionally the one or more flavoring agents;

(h) optionally the one or more viscosity enhancers;

(i) optionally the sodium hydroxide;

(j) optionally the sodium bicarbonate;

(k) optionally the sodium saccharinate;

(l) optionally the sodium benzoate; and (m) optionally the EDTA $Na_2$.

42. A pharmaceutical preparation as claimed in claim 40, wherein the at least one alcohol is selected from the group consisting of ethyl alcohol, glycerine, and a mixture of ethyl alcohol and glycerine.

43. A pharmaceutical preparation as claimed in claim 40, wherein the at least one alcohol is ethyl alcohol.

44. A pharmaceutical preparation as claimed in claim 40, wherein the water is present in the preparation at a second concentration of at least 72% w/v.

45. A pharmaceutical preparation as claimed in claim 40, wherein the first concentration ranges from 0.25 to 10% w/v.

46. A pharmaceutical preparation as claimed in claim 40, wherein the preparation is a mouthwash solution or tincture.

47. A method for treating inflammation of oral, pharyngeal, rhinopharyngeal, or laryngeal mucosa, the method comprising:

topically applying the pharmaceutical preparation claimed in claim 40, to the mucosa.

48. A pharmaceutical preparation as claimed in claim 41, wherein the at least one alcohol is selected from the group consisting of ethyl alcohol, glycerine, and a mixture of ethyl alcohol and glycerine.

49. A pharmaceutical preparation as claimed in claim 41, wherein the at least one alcohol is ethyl alcohol.

50. A pharmaceutical preparation as claimed in claim 48, wherein the water is present in the preparation at a second concentration of at least 72% w/v.

51. A pharmaceutical preparation a, claimed in claim 50, wherein the first concentration ranges from 0.25 to 10% w/v.

52. A pharmaceutical preparation as claimed in claim 50, wherein the preparation is a mouthwash solution or tincture.

53. A method for treating inflammation of oral, pharyngeal, rhinopharyngeal, or laryngeal mucosa, the method comprising:

topically applying the pharmaceutical preparation claimed in claim 50 to the mucosa.

54. A pharmaceutical preparation as claimed in claim 49, wherein the water is present in the preparation at a second concentration of at least 72% w/v; and wherein the first concentration ranges from 0.25 to 10% w/v.

* * * * *